US012779087B2

(12) United States Patent
Rompen et al.

(10) Patent No.: US 12,779,087 B2

(45) **Date of Patent: *Nov. 3, 2026**

(54) BONE REGENERATION MATERIAL

(71) Applicant: Wishbone, Flemalle (BE)

(72) Inventors: Eric Rompen, Liège (BE); Geoffrey Lecloux, Chaudfontaine (BE); France Lambert, Trooz (BE); Emilie Dory, Andenne (BE)

(73) Assignee: Wishbone, Flemalle (BE)

( * ) Notice: Subject to any disclaimer, the term of this patent is extended or adjusted under 35 U.S.C. 154(b) by 1057 days.

This patent is subject to a terminal disclaimer.

(21) Appl. No.: 17/560,316

(22) Filed: Dec. 23, 2021

(65) Prior Publication Data

US 2022/0111117 A1 Apr. 14, 2022

Related U.S. Application Data

(63) Continuation-in-part of application No. 16/477,904, filed as application No. PCT/EP2018/050877 on Jan. 15, 2018, now abandoned, which is a continuation-in-part of application No. PCT/EP2017/050779, filed on Jan. 16, 2017.

(30) Foreign Application Priority Data

Jan. 16, 2017 (BE) .................................. 2017/5025

(51) Int. Cl.

*A61L 27/12* (2006.01)
*A61F 2/28* (2006.01)
*A61L 27/36* (2006.01)

(52) U.S. Cl.

CPC ................ *A61L 27/12* (2013.01); *A61F 2/28* (2013.01); *A61L 27/3608* (2013.01); *A61L 27/365* (2013.01); *A61F 2002/2835* (2013.01); *A61L 2430/02* (2013.01)

(58) Field of Classification Search

None

See application file for complete search history.

(56) References Cited

U.S. PATENT DOCUMENTS

| | | | |
|---|---|---|---|
| 4,861,733 A | 8/1989 | White | |
| 5,417,975 A | 5/1995 | Lussi et al. | |
| 9,056,150 B2 * | 6/2015 | Gross | A61L 27/48 |
| 2003/0014124 A1 | 1/2003 | Wolfinbarger, Jr. et al. | |
| 2008/0249633 A1 | 10/2008 | Wu | |
| 2015/0024023 A1 | 1/2015 | Gibson et al. | |
| 2015/0098875 A1 | 4/2015 | Lee et al. | |
| 2016/0235885 A1 | 8/2016 | Rompen et al. | |
| 2020/0121827 A1 | 4/2020 | Dory et al. | |

FOREIGN PATENT DOCUMENTS

| | | |
|---|---|---|
| EP 0278583 | 8/1988 | |
| JP 2000-327314 | 11/2000 | |
| JP 2015-527125 | 9/2015 | |
| WO WO 96/12509 | 5/1996 | |

OTHER PUBLICATIONS

Decision on Appeal Dated Oct. 31, 2023 from the US Patent and Trademark Office Re. U.S. Appl. No. 16/477,904. (2 pages).

Official Action Dated May 28, 2021 from the US Patent and Trademark Office Re. U.S. Appl. No. 16/477,904. (17 pages).

Official Action Dated Nov. 9, 2020 from the US Patent and Trademark Office Re. U.S. Appl. No. 16/477,904. (18 pages).

Rapport de Recherche de Type Internationale et Opinion Ecrite [Search Report International and Written Opinion] Dated Jun. 6, 2014 From the European Patent Office Re. Application No. BE201300660. (9 Pages).

Rapport de Recherche Internationale et l'Opinion Ecrite [International Search Report and the Written Opinion] Dated Apr. 3, 2018 From the International Searching Authority Re. Application No. PCT/EP2018/050877. (8 Pages).

Restriction Official Action Dated Jun. 24, 2020 from the US Patent and Trademark Office Re. U.S. Appl. No. 16/477,904. (9 pages).

Brown et al. "Solubilities of Phosphates and Other Sparingly Soluble Compounds," National Bureau of Standards Report 10 599, May 28, 1971, 78 pages.

Fujiwara et el. "A Novel Strategy for Preparing Nanoporous Biphasic Calcium Phosphate of Controlled Composition via a Modified Nanoparticle—Assembly Method," Materials Science and Engineering: C, 35: 259-266, Feb. 1, 2014.

Harabi et al. "A Modified Milling System, Using a Bimodal Distribution of Highly Resistant Ceramics. Part 1. A Natural Hydroxyapatite Study," Materials Science and Engineering: C, 51: 206-215, Jun. 1, 2015.

(Continued)

*Primary Examiner* — David J Blanchard

*Assistant Examiner* — Daniel F Coughlin

(57) ABSTRACT

The present invention relates to a bone regeneration material comprising: a solid first phase of hydroxyapatite of natural origin which is macroporous, having pores of diameters greater than or equal to 50 μm, this phase of hydroxyapatite is a crystalline solid phase of hydroxyapatite, whose crystals have a size comprised between 20 and 120 nm, and this solid phase of hydroxyapatite has a specific surface area comprised between 8 and 20 $m^2/g$, the method of production and a method of bone repair based on this bone regeneration material.

25 Claims, 4 Drawing Sheets

(56) References Cited

OTHER PUBLICATIONS

Tang et al. "Fabrication, Characterization and Cellular Biocompatibility of Porous Biphasic Calcium Phosphate Bioceramic Scaffolds with Different Pore Sizes"; Ceramics International, 42(14): 15311-15318, Nov. 2016.
Bodhak et al. "Calcium Phosphate Coating on a Bioresorbable Hydroxyapatite/Collagen Nanocomposite for Surface Functionalization", Chemistry Letters, 42(9): 1029-1031, Published on Web Jun. 5, 2013.
Official Action Dated Jan. 19, 2022 from US Patent and Trademark Office Re. U.S. Appl. No. 16/477,904. (21 pages).
Official Action Dated Sep. 6, 2022 from US Patent and Trademark Office Re. U.S. Appl. No. 16/477,904. (21 pages).
Examiner answer in Response to the Appeal Brief Dated Aug. 16, 2023 Before the Patent Trial and Appeal Board of the US Patent and Trademark Office Re. U.S. Appl. No. 16/477,904. (14 pages).

* cited by examiner

BONE REGENERATION MATERIAL

RELATED APPLICATIONS

This application is a Continuation-in-Part (CIP) of U.S. patent application Ser. No. 16/477,904 filed on Jul. 15, 2019, which is a National Phase of PCT Patent Application No. PCT/EP2018/050877 having International filing date of Jan. 15, 2018, which is a Continuation-in-Part (CIP) of PCT Patent Application No. PCT/EP2017/050779 having International filing date of Jan. 16, 2017 and claims the benefit of priority of Belgium Patent Application No. BE2017/5025 filed on Jan. 16, 2017. The contents of the above applications are all incorporated by reference as if fully set forth herein in their entirety.

FIELD AND BACKGROUND OF THE INVENTION

The present invention relates to a bone regeneration material comprising a first solid phase of hydroxyapatite of natural origin which is macroporous having pores of diameters greater than or equal to 50 μm, preferably pores of diameters of between 50 and 100 μm.

The present invention further relates to a production process of the bone regeneration material consisting essentially of natural hydroxyapatite from natural origin and being macroporous.

The present invention finally relates to a method for reparation of a bone defect in a patient, comprising the use of the bone regeneration material consisting essentially of natural hydroxyapatite from natural origin and being microporous.

Such a bone regeneration material is known from document WO2015/049336 and is used as part of treating bone damage in different fields such as corrective or cosmetic surgery.

Hydroxyapatite is a mineral species from the phosphate family, of formula $Ca_5(PO_4)_3(OH)$. More specifically, hydroxyapatite belongs to the apatite crystallographic family which are isomorphic compounds having one same hexagonal structure. This compound is widely used as a biomaterial for many years in different medical specialities, as hydroxyapatites are the most frequent crystalline calcium phosphates, and the first mineral constituents of bones, tooth enamel and dentine. Moreover, hydroxyapatites (and in particular, hydroxyapatites of natural origin) have good biocompatibility and specific adsorption properties of cells or proteins.

It is thus recognised that hydroxyapatite of natural origin has osteoconductive properties as well as a crystalline structure and a morphology identical to those of a natural bone material in humans, hydroxyapatite consequently perfectly suiting as part of a bone reconstructive or corrective surgery. In this sense, numerous materials comprising hydroxyapatite are currently used as dental implants to stimulate the bone reconstruction on bone sites having defects or damage. In particular, using a natural hydroxyapatite coming from bone samples cleaned of the organic substances thereof (proteins, prions, peptides and lipids) makes it possible to obtain a matrix, particularly specific to bone regeneration compared with the artificial analogue thereof. It is preferable that the bone regeneration material is purified beforehand of any trace of organic substances such that the implant is correctly accepted/integrated by the organism, is biocompatible and can interact by osteoconduction with the biological medium wherein it is placed.

As examples, hydroxyapatites can be used as substitution materials to replace or regenerate diseased or damaged tissues. They are also frequently used as a coating on titanium protheses to facilitate the osteointegration or also can prevent wear due to micromovements between the implant and the bone. Hydroxyapatites can also be used as cement in order to replace autogenic bone grafts. Furthermore, a growing number of hydroxyapatite applications as a medication vector is developed, this because hydroxyapatite has a structure with interconnected micropores.

As mentioned above, hydroxyapatite has a chemical composition very close to that of the mineral phase of the bone and the biological properties thereof as well as the biocompatibility thereof make it an excellent bone substitution product. It is specified that a bone colonisation depends on the porous characteristics of the bone regeneration material and the interconnection between the macropores thereof (number and dimension). These interconnections constitute types of "tunnels" which make it possible for the passage of cells and blood circulation between the pores thus encouraging bone formation.

Hydroxyapatite, through the high biocompatibility level thereof and the slow resorption thereof in the organism, can be administered in different forms and in numerous tissues for various applications. In particular, hydroxyapatite-based malleable cements are distinguished which are prepared then administered on the zone to be treated where they harden. These cements are used as a bone substitute due to the good osteointegration thereof and the bioresorbability thereof making it possible to give way to a neoformed bone over time.

There are also solutions and hydroxyapatite-based gels which can contain a polymer such as carboxymethylcellulose. Thus, bioactive ceramic-polymer composite implants are spoken of, these products can be used in different fields such as to fill periodontal deficiencies in dental surgery or carry out fillings in orthopaedic surgery.

Certain hydroxyapatite-based products are also presented in the form of a block, powder or granules used in orthopaedics, fillings or as a complement to dental implants.

Among hydroxyapatite-based products, numerous are those which are not ready for use and which require a preparation beforehand. It is the case, in particular, for hydroxyapatite-based cements which require a prior mixing of a powder and a solution before deposition on or in a zone to be treated where an in situ hardening is thus carried out. Other hydroxyapatite-based products also require to be shaped before implantation on or in the zone to be treated.

Unfortunately, even if such a bone regeneration material comprising a solid phase of hydroxyapatite of natural origin which is macroporous has properties specific to an endo-osseous implantation and makes it possible for a correct bone regeneration thanks to the biocompatibility thereof and to the osteoconductive capacities thereof, it is observed, in practice, that this type of bone regeneration material is not always optimal and that the timeframe for the bone regeneration process is always relatively long (1 mm/month). Moreover, the bone regeneration quantity is frequently insufficient, which leads to the formation of partial fibroses rather than a total ossification.

With the aim of accelerating the bone regeneration process, document US2002/0114755 discloses a material comprising hydroxyapatite and 50 to 90% by mass of tricalcium phosphate, the material according to this prior document being obtained by converting hard algal tissues in an aqueous phosphate solution with the addition of $Mg^{++}$ ions at an increased temperature.

The bone regeneration material according to this prior document, i.e. which comprises hydroxyapatite and 50 to 90% by mass of tricalcium phosphate of natural origin, has an interconnected porous structure, an improved and controllable resorption in the organism leading to an accelerated bone regeneration.

Unfortunately, even if a bone regeneration material according to document US2002/0114755 makes it possible to accelerate the bone regeneration process by increasing the calcium and phosphorus contribution in the form of free ions in the direct medium of the implantation site, it is observed that this type of material is not optimal.

Indeed, the method for obtaining such a bone regeneration material consists of transforming hydroxyapatite into tricalcium phosphate. Therefore, this is the conversion of a first natural phase into a second natural phase, hydroxyapatite being replaced with tricalcium phosphate.

Thus, during the implantation of the bone regeneration material according to document US2002/0114755, tricalcium phosphate which is more soluble than hydroxyapatite will quickly be solubilised and release calcium and phosphorous ions in the medium of the implantation site. As mentioned above, the tricalcium phosphate of such a bone regeneration material represents 50 to 90% by mass and is obtained by the conversion of a portion of hydroxyapatite contained in the starting material, namely the hard algal tissue. Consequently, with a bone regeneration material according to this prior document, 50 to 90% of the mass (corresponding to tricalcium phosphate) will quickly be solubilised following the implantation and thus lead to a natural hydroxyapatite material having wide empty zones and therefore to a hydroxyapatite material which is certainly of natural origin but which no longer has optimal topographic characteristics (porosity, specific surface area, etc.) making it possible for a good bone regeneration.

A bone regeneration material according to document US2002/0114755 therefore does not make it possible to maintain, over the long term, the suitable microporous structure of natural hydroxyapatite once this implanted and does not therefore make it possible to ensure an optimal bone regeneration process on the implantation site in terms of proliferation and differentiation of bone cells as such a material, once implanted, no longer has a superficial topography, nor a suitable microporosity.

Unfortunately, although the above products present several advantageous properties, the inventors do consider that their mechanical resistance should be improved.

SUMMARY OF THE INVENTION

The invention aims to overcome the disadvantages of the state of the art by providing a bone regeneration material making it possible to minimise the bone regeneration time while stimulating the bone regeneration potential so as to obtain an optimal regenerated bone quantity. Also, the present invention discloses a bone regeneration material as described here above, with the solid hydroxyapatite phase, being crystalline hydroxyapatite having a specific surface area between 8 and 20 $m^2/g$ and wherein the crystals have a size comprised between 20 and 120 nm.

Advantageously, the bone regeneration material has been obtained after a (mild) sintering step at a temperature comprised between 800° C. and 1200° C., preferably between 800° C. and 1150° C., preferably between 800° C. and 1100° C. (or 1000° C. or 950° C. or 900° C. or 850° C.), advantageously at a temperature between 810° C. and 830° C., such as (about) 820° C.

Such a sintering step allows, among others, to “weld” crystals of the solid hydroxyapatite phase from a natural origin, causing a strong reduction (possibly a total suppression) of nanopores and of micropores, together with an increase of the crystal size and a reduction of the specific surface. However, the strong reduction (or the total suppression) of the nanopores and/or of the micropores of the bone regeneration material is considered as prejudicial since the vascularization and the colonization of the material will be no longer possible or hampered; hence the subsequent bone regeneration risks to be incomplete or with a reduced quality.

It is, indeed, widely recognized that the absence of microporosity within a bone regeneration material is detrimental with regard to bone generation and growth and to osteoconduction.

Against this prejudice, the sintering step according to the present invention is particularly advantageous since it allows to maintain surface topography of the bone regeneration material, which saves the bone regeneration potential and increases its mechanical strength.

For instance, the sintering step of the bone regeneration material according to the present invention allows to form elements almost spherical at the surface of the bone regeneration material.

Thus, the bone regeneration material harbours spherical-like/ball-like elements of a size (diameter or equivalent diameter) comprised between 150 and 350 nm, preferably between 175 and 325 nm, or between 200 and 300 nm. The spherical/ball-like elements form together a rough surface. Conversely, a sintering step above 1200° C. will trigger “melting” of the hydroxyapatite at the surface of the bone regeneration material, forming a too smooth surface, hampering the bone regeneration potential.

Surprisingly, the inventors have remarked that the bone regeneration material according to the present invention, i.e. after a (mild and/or controlled) sintering step, and wherein the crystals of the hydroxyapatite phase have a size comprised between 20 and 120 nm and having a specific surface between 8 and 20 $m^2/g$, is colonized by the bone tissues as efficiently as the prior art materials, but have a more rigid and resistant structure, and keeping the rough surface topography.

Indeed, the bone regeneration material is considered for an implantation or the reconstruction and/or regeneration of a bone defect or damage, more particularly of the masticatory apparatus, where the applied constraints upon mastication are very strong and repeated over the time.

Such a bone regeneration material is thus particularly advantageous since it harbours similar features and advantages as in the prior art with regard to the bone regeneration, osteointegration and osteoconduction potentials and it is more rigid and resistant: its surface roughness keeps, or even improves, the bone regeneration potential.

Advantageously, the crystals of the solid phase hydroxyapatite of the bone regeneration material according to the present invention have a size comprised between 30 and 120 nm, preferably between 40 and 100 nm, preferably between 45 and 80 nm, more preferably between 50 and 80 nm, advantageously between 50 and 60 nm.

Advantageously, the specific surface area of the solid phase hydroxyapatite of the bone regeneration material according to the present invention is comprised between 10 and 20 $m^2/g$, preferably between 10 and 18 $m^2/g$, more preferably between 12 and 16 $m^2/g$.

Preferably, the bone regeneration material according to the present invention has a porosity comprised between 70 and 85%, preferably between 75 and 85%, more preferably between 80 and 85%. This allows an increased potential for bone regeneration.

Preferably, the bone regeneration material according to the present invention has a granulometric distribution $d_{10}$ comprised between 350 and 500 μm, preferably between 370 and 480 μm.

Preferably, the bone regeneration material according to the present invention has a granulometric distribution $d_{50}$ comprised between 500 and 800 μm, preferably between 550 and 780 μm.

Preferably, the bone regeneration material according to the present invention has a granulometric distribution $d_{90}$ comprised between 850 and 1250 μm, preferably between 850 and 1100 μm, more preferably between 850 and 1000 μm.

These granulometric distributions allow an optimal porous volume for bone regeneration.

The bone regeneration material according to the invention not only has chemical properties (optimised calcium and phosphorus salting-out in the form of free ions) which make it possible to minimise the bone regeneration time, but also has optimal physical properties (topography and porosity conserved) enabling a good bone colonisation so as to obtain an optimal regenerated bone quantity.

To resolve this problem, a second and/or complementary bone regeneration material according to the invention is provided, comprising a first solid phase of hydroxyapatite of natural origin which is macroporous having pores of diameters greater than or equal to 50 μm, preferably pores of diameters of between 50 and 100 μm, said bone regeneration material, the bone regeneration material according to the invention being characterised in that it further comprises a second solid synthetic phase of calcium phosphate intended to enrich said first phase, said second phase having a Ca/P molar ratio of between 0.2 and 2, preferably of between 0.3 and 1.8, preferably between 0.5 and 1.65, said bone regeneration material having a defined weight ratio between said first solid phase of hydroxyapatite of natural origin and said second solid synthetic phase of calcium phosphate of between 99/1 and 1/99.

Advantageously, according to the invention, the defined weight ratio between said first solid phase of hydroxyapatite of natural origin and said second solid synthetic phase of calcium phosphate is 95/5, 90/10, 85/15, 80/20, 75/25, 70/30, 65/35, 60/40, 55/45, 50/50, 45/55, 40/60, 35/65, 30/70, 25/75, 20/80, 15/85, 10/90 or 5/95.

In the scope of the present invention, it has been highlighted that such a bone regeneration material according to the invention having:

- a first solid phase of hydroxyapatite of natural origin having pores of diameters greater than or equal to 50 μm, preferably pores of diameters of between 50 and 100 μm;
- a second solid synthetic phase of calcium phosphate intended to enrich said first phase;
- a Ca/P molar ratio for the second solid synthetic phase of calcium phosphate of between 0.2 and 2, preferably of between 0.3 and 1.8, preferably of between 0.5 and 1.65; and
- a defined weight ratio between said first solid phase of hydroxyapatite of natural origin and said second synthetic solid phase of calcium phosphate of between 99/1 and 1/99, makes it possible to ensure a suitable salting-out of calcium (for example, in the form of extracellular free $Ca^{2+}$ ions) and phosphorus (for example, in the form of extracellular free $PO_4^{3-}$ ions) in the medium of the bone regeneration site such that these can play the role of promoters of the regrowth of surrounding biological tissues by significantly encouraging the proliferation and the differentiation of bone cells as well as mineralisation.

Furthermore, it has been observed, surprisingly, that the bone regeneration material according to the invention, i.e. of which the solid phase of hydroxyapatite is a natural phase of hydroxyapatite which is enriched by a second phase of calcium phosphate, has optimal topographic characteristics (porosity, specific surface area, etc.) making it possible to optimise the bone regeneration by enabling a good bone colonisation, and this even after the implantation of the bone regeneration material.

A good bone colonisation depends on the porous characteristics of the bone generation material and the interconnection between the macropores thereof (number and dimensions), these interconnections constituting types of "tunnels", which make it possible for the passage of cells and blood circulation between the pores encouraging bone formation. The conservation of the topographic characteristics of natural hydroxyapatite is therefore paramount to obtain a suitable bone regeneration, which is not the case with a regeneration material according to document US2002/0114755 where a portion (50 to 90% by mass) of the natural phase of hydroxyapatite is converted into a natural phase of tricalcium phosphate.

A bone regeneration material according to the invention therefore has both optimal chemical and physical properties (optimised calcium and phosphorus salting-out in the form of free ions/topography, porosity) which ensure a bone regeneration and a formation of the bone optimised in a significantly reduced time with respect to a bone regeneration material such as that of documents WO2015/049336 and US2002/0114755.

In particular, in the scope of the present invention, it has been highlighted that, when the defined weight ratio between said first solid phase of hydroxyapatite of natural origin and said second synthetic solid phase of calcium phosphate is of between 99/1 and 1/99, and is preferably 95/5, 90/10, 85/15, 80/20, 75/25, 70/30, 65/35, 60/40, 55/45, 50/50, 45/55, 40/60, 35/65, 30/70, 25/75, 20/80, 15/85, 10/90 or 5/95, the bone regeneration time is significantly reduced. This is due to the fact that with such a ratio, at least one of the calcium and/or phosphorus salting-outs in the form of free ions is such that calcium and/or phosphorus is thus located in the surrounding bone regeneration medium in a quantity making it possible to significantly increase the concentration here with respect to the concentration naturally encountered, while only hydroxyapatite tends to capture calcium and phosphorus in the form of free ions and to deplete the surrounding medium thereof from the bone regeneration site.

It must be noted, that two-phase bone regeneration materials are described in the state of the art, in particular materials consisting of a synthetic hydroxyapatite and synthetic tricalcium calcium phosphate association: these are therefore 100% synthetic materials which, as for a regeneration material such as indicated at the start, impose a relatively long bone regeneration duration. Moreover, such totally synthetic two-phase bone regeneration materials do not make it possible, on the contrary, for a material according to the invention, to ensure an optimal bone regeneration on the implantation site in terms of proliferation and differentiation of bone cells as they do not have a suitable superficial topography nor a suitable microporosity.

Preferably, according to the invention, said second synthetic solid phase of calcium phosphate has a Ks solubility product greater than that of said first phase of hydroxyapatite of natural origin. This is particularly advantageous, since calcium and phosphorus must be contributed in the form of free ions in the direct medium of the implantation site while conserving the structural properties (pore size, specific surface area, etc.) and composition of the solid phase of hydroxyapatite of natural origin. Since the solubility of the second phase is greater, it is mainly this phase in particular which will be at the origin of the calcium and phosphorus release in the form of free ions (for example, $Ca^{2+}$ and $PO_4^{3-}$) and not hydroxyapatite of natural origin, which is clearly less dissolved and which, on the contrary, tends to fix these ions at the start of the implantation medium.

Advantageously, according to the invention, said first solid phase of hydroxyapatite of natural origin has a specific surface area greater than 4 $m^2/g$.

Preferably, according to the invention, said second synthetic solid phase of calcium phosphate is selected from the group constituted of monocalcium calcium phosphate (MCP), dicalcium calcium phosphate (DCP), octacalcium phosphate (OCP), calcium deficient apatite (CDA), amorphous calcium phosphate (ACP), tricalcium calcium phosphate (TCP), tetracalcium calcium phosphate (TTCP), and the mixtures thereof.

Advantageously, according to the invention, said first phase of hydroxyapatite of natural origin is hydroxyapatite obtained from a bone material of natural origin, in particular from a bone material of animal origin. For example, hydroxyapatite of natural origin can be hydroxyapatite obtained from a bone material coming from a mammal (bovine, horse, pig or sheep), coral or dry.

Preferably, according to the invention, said hydroxyapatite of natural origin which is macroporous of said first phase is a hydroxyapatite of natural origin which is macroporous at least partially sintered. The controlled sintering (heating of a powder without leading it to melt) advantageously makes it possible to obtain a hydroxyapatite of natural origin having increased mechanical resistance properties while conserving a suitable microporosity and a suitable surface topography, which makes it possible to facilitate the implantation and to improve the long-term stability after implantation.

Advantageously, the bone regeneration material according to the invention, further comprises at least one therapeutic agent selected in the group constituted of antibiotics, antivirals, anti-inflammatories, hormones such as steroids, growth factors such as BMPs (Bone Morphogenetic Proteins), anti-rejection agents, stem cells, and the mixtures thereof.

Preferably, the bone regeneration material according to the invention is intended to be used as an implant or prothesis for a bone formation, a bone regeneration or for a bone correction in a mammal, preferably in a human.

Other embodiments of a bone regeneration material according to the invention are indicated in the appended claims.

The inventions also aims for a medical device containing a bone regeneration material according to the invention.

Other embodiments of a medical device according to the invention are indicated in the appended claims.

The invention also aims for a bone regeneration composition comprising a bone regeneration material according to the invention.

Other embodiments of a composition according to the invention are indicated in the appended claims.

The present invention is also based on a method for producing a bone regeneration material (according to the present invention) comprising:

- contacting the bone material, comprising hydroxyapatite and organic substances with an aqueous extraction solution at a temperature between 150° C. and 300° C. and at a pressure comprised between 1500 kPa and 3500 kPa, so as to obtain a first liquid phase comprising said organic substances and possibly impurities extracted from said bone material and a second phase of solid hydroxyapatite;
- separating the liquid phase from the hydroxyapatite solid phase;
- sintering the hydroxyapatite solid phase at a temperature comprised between 800° C. and 1200° C.;
- the said hydroxyapatite solid phase forming the said bone regeneration material.

This advantageously allows a sintered bone regeneration material having at least the same (advantageous) properties of bone regeneration potential, osteointegration and osteoconduction as in the prior art, and an increased rigidity and resistance, with a surface roughness that keeps, or even improves, the bone regeneration potential.

Sintering temperatures lower than 800° C. do not allow the increase of the mechanical resistance, whereas temperatures higher than 1200° C. or even higher than 900° C. negatively impact the surface topography and the bone regeneration potential: sintering conditions between 800° C. and (900° C.) 1200° C. allow to obtain a bone regeneration material that is solid, robust, resistant and which allows the desired bone regeneration potential so as to be implantable for a patient.

This process can be combined with a sieving step of the solid phase hydroxyapatite on a series of sieves, after the separation step and before the sintering step, preferably a first sieving substep on a 1 mm sieve (mesh) and at least a second sieving step on a 0.25 mm sieve (mesh).

Advantageously, rolling balls can be added on the sieves and these balls can be moved on the surface of the sieves: this will weaken the solid phase hydroxyapatite, increasing the passing of the hydroxyapatite particles (of a desired size) and increasing the production of hydroxyapatite particles of the desired size.

Advantageously, just after the sieving step, a bleaching step with (hydrogen) peroxide can be performed, for instance an aqueous composition comprising the peroxide, optionally followed by a (gentle) drying step.

Advantageously, the temperature of the aqueous extraction solution is comprised between 170° C. and 280° C., preferably between 190° C. and 260° C., more preferably between 210° C. and 240° C., advantageously between 220° C. and 230° C.

Preferably, the pressure of the aqueous extraction solution is comprised between 2000 and 3500 kPa, preferably between 2500 and 3500 kPa, more preferably between 3000 and 3500 kPa, advantageously between 3200 and 3500 kPa, such as between 3400 and 3500 kPa.

Such a supercritical extraction according to the invention and meeting the above conditions, such as a temperature between 220 and 230° C. and a pressure between 3200 and 3500 kPa, delivers the best results for the generation of a pure hydroxyapatite solid phase, which is cleaned from organic substances (e.g. proteins, prions, peptides, lipid), thereby reducing the deleterious rejection reactions, which risk otherwise to occur.

The duration of the supercritical extraction step is advantageously adapted according to the quantity of the bone material.

Advantageously, the sintering step is performed for a time comprised between 40 minutes and 4 hours, preferably between 1 and 3 hours, preferably between 1 and 2 hours, such as between 1 and 1.5 hour (90 minutes).

This sintering step comprises advantageously a sub-step of temperature increase, followed by a sub step at a plateau temperature (the final designed temperature comprised between 800° C. and 1200° C. or 900° C., such as between 800° C. and 850° C. or between 810° C. and 830° C., as above).

Preferably, the sub-step of temperature increase allows to reach the designed temperature in a period comprised between 20 minutes and 2 hours, preferably between 20 minutes and 1 hour, more preferably between 20 minutes and 45 minutes, such as between 25 and 35 minutes.

An advantageous sub-step allows to reach a temperature of 820° C. in 30 minutes.

Preferably, during the temperature increase sub-step, the temperature increase is substantially linear in function of the elapsed time.

This allows a rapid and/or reproducible sub-step of temperature increase.

Indeed, the inventors have observed that too long durations of this sub-step of temperature increase, especially when the temperature exceeds 600° C., already start to affect the bone material, which is not necessarily fatal or deleterious, but must be taken into account when designing the second sub-step of the plateau phase at a temperature comprised between 800° C. and 1200° C. (or 900° C.), such as between 810° C. and 830° C.

Moreover, the sub-step of the temperature plateau of the sintering step at a temperature comprised between 800° C. and 1200° C. (or 900° C.), such as between 810° C. and 830° C. is advantageously performed for a period comprised between 20 minutes and 2 hours, preferably between 30 minutes and 90 minutes, preferably between 45 minutes and 1 hour, such as between 46 minutes and 58 minutes.

For example, the sub-step of temperature plateau is performed at 820° C. for a duration comprised between 45 and 58 minutes.

Moreover, some flexibility is offered with regard to the temperature and the duration of the sintering step. However, the inventors have found that the temperature of the plateau phase is the most important parameter and is the main parameter to control.

The present invention is also based on a method for enriching a bone regeneration material according to the invention, said method comprising:

- a step of supplying a bone regeneration material (e.g. the bone material after the extraction step and the separation step as above, possibly also after the sieving step, if performed, or even after the sintering step), and
- a step (before the mild and/or the controlled sintering step at a temperature between 800° C. and 1200° C. or between 800° C. and 900° C., or even after this sintering step, and as above) of enriching said bone regeneration material, in calcium and in phosphorus, said method being characterised in that said calcium and phosphorus enriching step is carried out by at least one first and at least one second separate soaking succeeding one another in any order, said at least one first soaking taking place in a first solution comprising calcium and said at least one second soaking taking place in a second solution comprising phosphorus.

Preferably, according to the method according to the invention, said first soaking takes place in a first solution of $Ca(NO_3)_2.4H_2O$, of $CaCl_2.2H_2O$, of $Ca(OH)_2$, $CaSO_4.2H_2O$, or of $CaCO_3$.

Advantageously, according to the method according to the invention, said second soaking takes place in a second solution of $Na_3PO_4$, of $Na_2HPO_4$, of $NaH_2PO_4.H_2O$, of $K_3PO_4$ of $K_2HPO_4$, of $KH_2PO_4$, of $K_2HPO_4$, of $(NH_4)_3PO_4$, of $(NH_4)_2HPO_4$ or of $NH_4H_2PO_4$.

The present invention also discloses a reparation method of a bone defect in a patient comprising the steps of:

- measuring the size of the defect to correct;
- placing a synthetic bone regeneration device arranged to increase bone regeneration in the bone defect, being obtained by 3D printing and comprising at least one shell made of a porous matrix and presenting pores having a size comprised between 50 and 1000 μm, and at least a holder shaft bound on this porous matrix and on the bone surface of this bone defect, this device being arranged so as to encompass an empty zone, which is arranged to house a bone volume to regenerate,
- filling this empty zone formed by this device by the bone regeneration material according to the present invention.

This is especially useful for repairing defects at bones under strong mechanical constraints, such as bones of the masticatory apparatus.

Other embodiments of a method according to the invention are indicated in the appended claims.

Other characteristics, details and advantages of the invention will emerge from the description given below, in a non-limiting manner and by making reference to the appended figures.

DESCRIPTION OF SPECIFIC EMBODIMENTS OF THE INVENTION

Examples

Figure 1A:
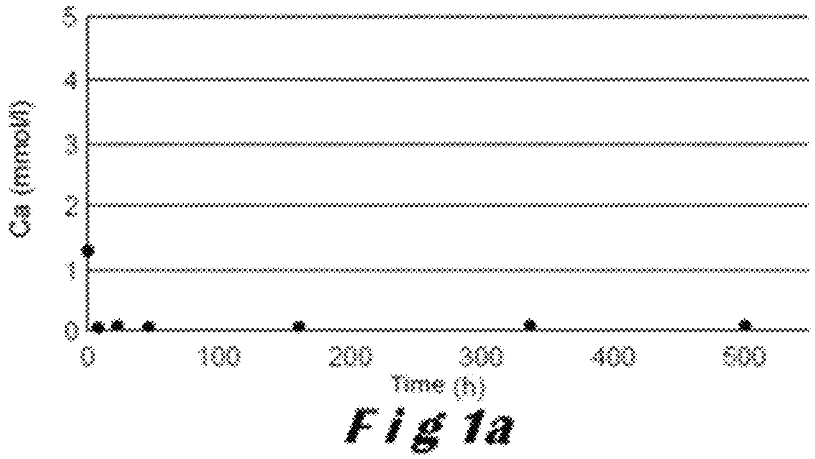
FIGS. 1*a*, 1*b* and 1*c* illustrate respectively the development of the calcium (Ca) concentration over time for a solid phase of hydroxyapatite of natural bovine origin, non-enriched, immersed in an HBSS medium, the development of the phosphorus (P) concentration over time for a solid phase of hydroxyapatite of natural bovine origin, non-enriched, immersed in an HBSS medium, and the weight increase over time for a solid phase of hydroxyapatite of natural bovine origin, non-enriched, immersed in an HBSS medium.

Comparison of Calcium and Phosphorus Salting-Outs in the Form of Free Ions Over Time for Different Bone Regeneration Materials—Solubility Tests Comparative tests have been carried out in order to determine the calcium and phosphorus quantities (concentrations) salted-out over time (solubility tests) at the start of different bone regeneration materials, this in an medium reproducing the in vivo implantation conditions.

1. Methodology

To do this, the calcium and phosphorus ratios and quantities (concentrations) salted-out have been measured in a medium simulating the in vivo implantation conditions (human blood plasma), i.e. in an HBSS medium (Hank's balanced salt medium) having a pH of 7 and of which the composition is outlined in table 1 below:

TABLE 1

| | Concentrations (mM) |
|---|---|
| $Na^+$ | 142.8 |
| $K^+$ | 5.8 |
| $Mg^{2+}$ | 0.9 |
| $Ca^{2+}$ | 1.3 |
| $Cl^-$ | 146.8 |
| $HCO^{3-}$ | 4.2 |
| $HPO_4^{2-}$ | 0.3 |
| $H_2PO^{4-}$ | 0.4 |
| $SO_4^{2-}$ | 0.4 |
| Glucose | 5.6 |

The following bone regeneration materials have been tested:

Material 1: 0.5 g of solid phase of hydroxyapatite of natural bovine origin, non-enriched, having pores of a size of between 50 and 100 μm;

Material 2: 0.5 g of solid phase of hydroxyapatite of natural bovine origin having pores of a size of between 50 and 100 μm and enriched by a synthetic solid phase of calcium phosphate according to a ratio by weight of solid phase of hydroxyapatite/synthetic solid phase of calcium phosphate of 90/10, the phase of calcium phosphate having a Ca/P molar ratio of less than 1.67; and Material 3: 0.5 g of solid phase of hydroxyapatite of natural bovine origin having pores of a size of between 50 and 100 μm and enriched by a synthetic solid phase of calcium phosphate according to a ratio by weight of solid phase of hydroxyapatite/synthetic solid phase of calcium phosphate of 80/20, the phase of calcium phosphate having a Ca/P molar ratio of less than 1.67.

The solid phase of hydroxyapatite of natural bovine origin is obtained according to the method described in document WO2015/049336 and is more specifically composed of hydroxyapatite particles having a size of between 0.25 mm and 1 mm.

The materials comprising a first solid phase of hydroxyapatite of natural origin and a second synthetic solid phase of calcium phosphate have been obtained by successive and alternate soakings for a duration of 5 minutes of the first solid phase of hydroxyapatite of natural origin (hydroxyapatite particles) in separate baths of $Ca(NO_3)_2.4H_2O$ (1M, pH=10) and of $NaH_2PO_4.H_2O$ (0.5M, pH=10). The first bath makes it possible to enrich the hydroxyapatite calcium ($Ca^{2+}$) particles of natural origin, the second phosphorus ($PO_4^{3-}$) bath. Following 4 successive soakings (2 soakings in each bath) to obtain a ratio by weight of solid phase of hydroxyapatite/synthetic solid phase of calcium phosphate of 90/10 or following 6 successive soakings (3 soakings in each bath) to obtain a ratio by weight of solid phase of hydroxyapatite/synthetic solid phase of calcium phosphate of 80/20, the hydroxyapatite particles of natural origin enriched in calcium and in phosphorus have been rinsed in order to remove the excess calcium and phosphorus then dried at a temperature of 100° C. for 6 hours.

A total of 36 samples (of 0.5 g) have been tested simultaneously by immersing in 10 ml of HBSS medium at a temperature of 37° C. Calcium and phosphorus salting-out measurements in the form of free ions have been taken after 8 hours, 24 hours, 48 hours, 1 week, 2 weeks and 3 weeks on two samples for each material and by duration, these samples being rinsed and dried at a temperature of 100° C. after each of these durations.

The calcium and phosphorus quantities (concentrations) salted-out at the start of each sample in the HBSS medium have been measured according to the ICP-AES (Inductively Coupled Plasma—Atomic Emission Spectroscopy) technique, this following a removal of possible materials suspended in the HBSS medium by centrifugation. The weight of the materials have been defined by weighing (gravimetry) before and after immersion in the HBSS medium, this for each of the durations mentioned above.

2. Results

The results obtained are illustrated in FIGS. 1 to 3. For each of the materials (samples), the starting calcium and phosphorus concentrations are respectively 1.26 mmol/l and 0.78 mmol/l, which corresponds to the concentrations of these ions in the initial HBSS medium.

Figure 1B:
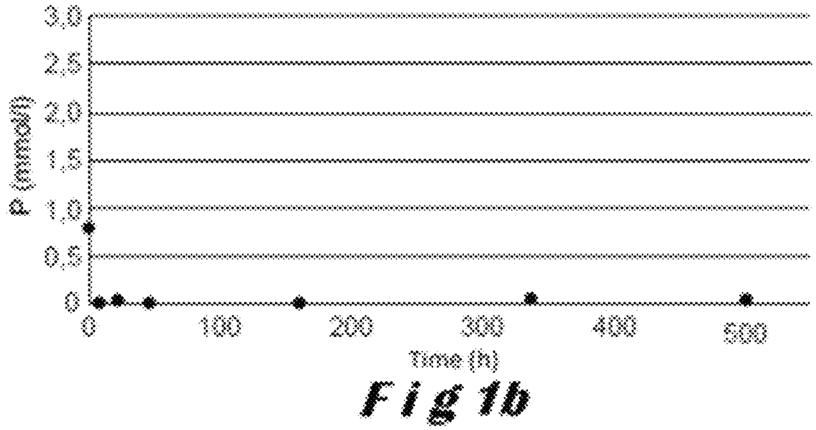
Figure 1C:
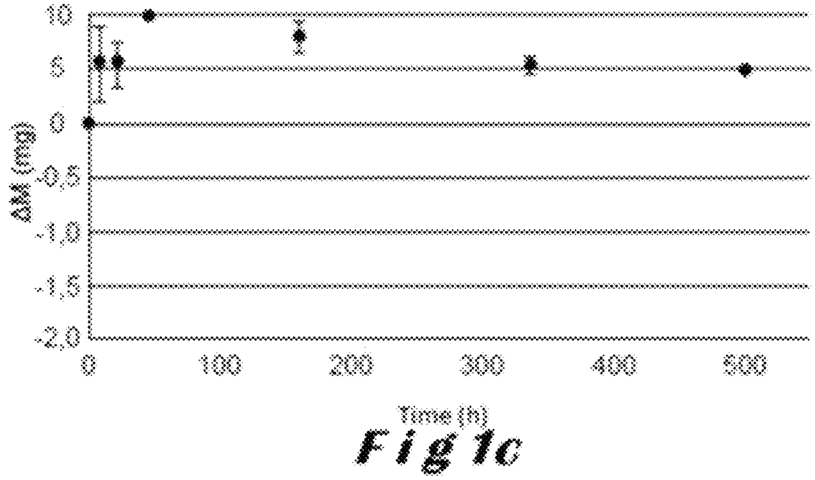
Figure 2A:
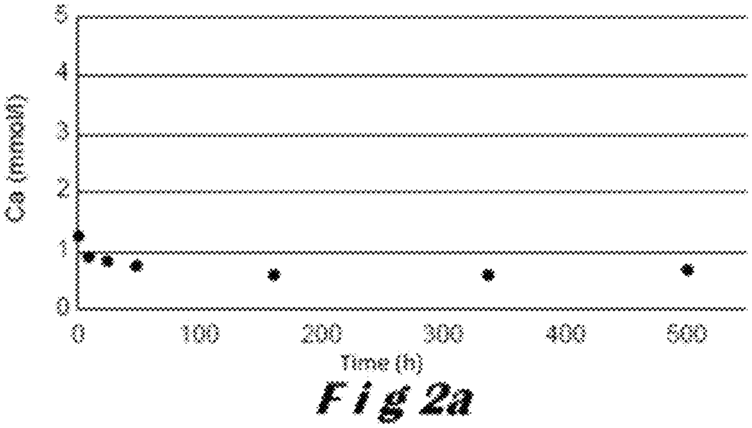
FIGS. 2*a*, 2*b* and 2*c* illustrate respectively the development of the calcium (Ca) concentration over time for a material immersed in an HBSS medium and comprising a solid phase of hydroxyapatite of natural bovine origin enriched by a synthetic solid phase of calcium phosphate (ratio 90/10), the development of the phosphorus (P) concentration over time for a material immersed in an HBSS medium and comprising a solid phase of hydroxyapatite of natural bovine origin enriched by a synthetic solid phase of calcium phosphate (ratio 90/10) and the weight increase for a material immersed in an HBSS medium and comprising a solid phase of hydroxyapatite of natural bovine origin enriched by a synthetic solid phase of calcium phosphate (ratio 90/10).
Figure 2B:
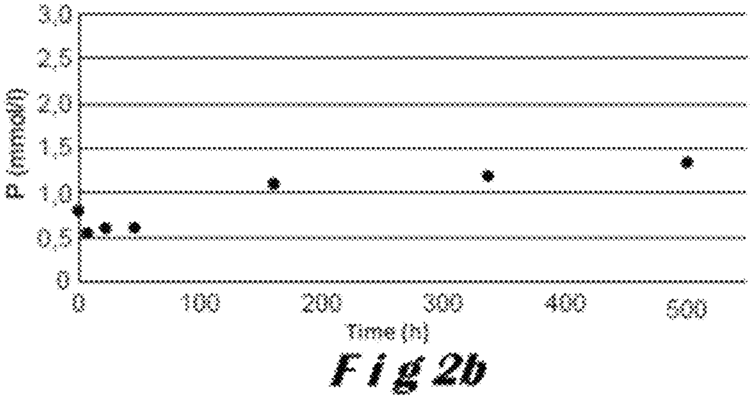

These results show that, when the material 1—solid phase of hydroxyapatite of natural bovine origin, non-enriched—is immersed in the HBSS medium, the calcium and phosphorus concentrations in the form of free ions decrease before being stabilised (FIGS. 1*a* and 1*b*). At the same time, an increase by weight of the material 1 is observed (FIG. 1*c*). For example, after 3 weeks, the calcium concentration in the medium is 0.06 mmol/l while the phosphorus concentration in the medium is 0.03 mmol/l for an average weight increase per sample of 5 mg.

Figure 2C:
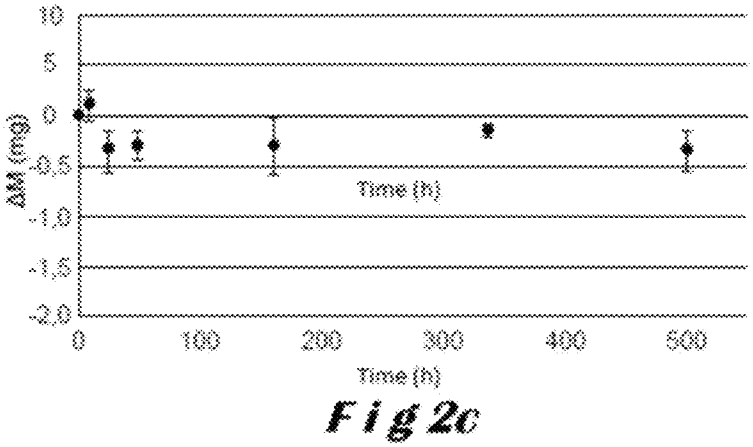

For the material 2—solid phase of hydroxyapatite of natural bovine origin enriched by a synthetic solid calcium phase (ratio 90/10)—the calcium and phosphorus concentrations start by decreasing with a quick stabilisation of the calcium concentration (0.6 mmol/l) while the phosphorus concentration progressively increases up to reaching a final value of 1.34 mmol/l after 3 weeks of immersion (FIGS. 2*a* and 2*b*), this concentration being greater than the initial phosphorus concentration in the HBSS medium. The weights of the samples of the material 2 have first barely increased before decreasing down to a loss by weight of 3.5 mg (FIG. 2*c*).

Figure 3A:
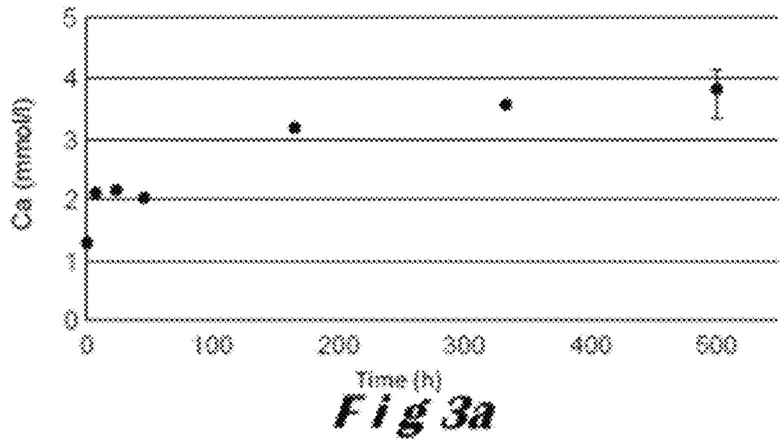
FIGS. 3*a*, 3*b* and 3*c* illustrate respectively the development of the calcium (Ca) concentration over time for a material immersed in an HBSS medium and comprising a solid phase of hydroxyapatite of natural bovine origin enriched by a synthetic solid phase of calcium phosphate (ratio 80/20), the development of the phosphorus (P) concentration over time for a material immersed in an HBSS medium and comprising a solid phase of hydroxyapatite of natural bovine origin enriched by a synthetic solid phase of calcium phosphate (ratio 80/20) and the weight increase for a material immersed in an HBSS medium and comprising a solid phase of hydroxyapatite of natural bovine origin enriched by a synthetic solid phase of calcium phosphate (ratio 80/20).
Figure 3B:
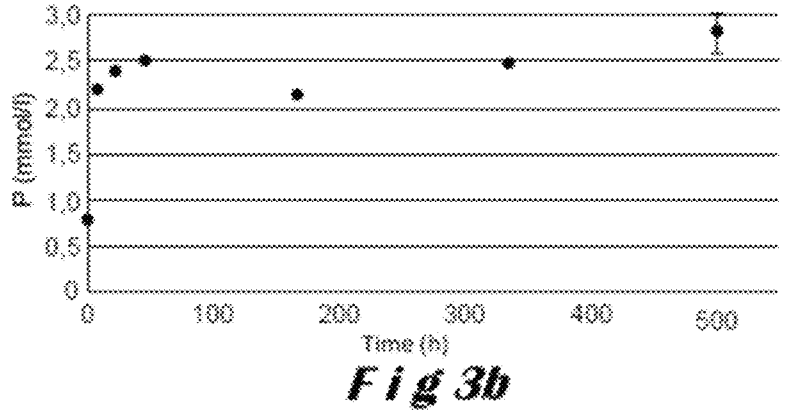
Figure 3C:
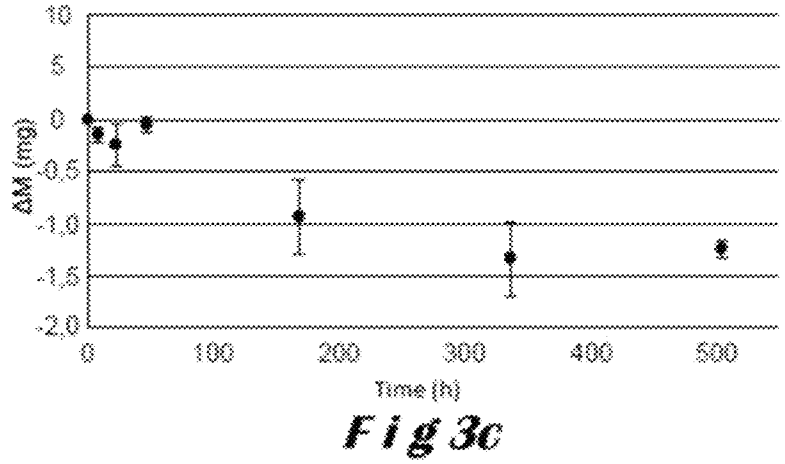

Concerning the material 3—solid phase of hydroxyapatite of natural bovine origin enriched by a synthetic solid phase of calcium phosphate (ratio 80/20)—the calcium and phosphorus concentrations increase over time while the weights of the samples decreases (FIGS. 3*a* to 3*c*). The final calcium and phosphorus concentrations, after 3 weeks of immersion in the HBSS medium, are respectively 3.69 mmol/l and 2.78 mmol/l for a loss by weight of 12.5 mg, these concentrations being greater than those initially measured in the HBSS medium.

3. Conclusion

The results obtained with the material 1—solid phase of hydroxyapatite of natural bovine origin, non-enriched—highlight the capacity of hydroxyapatite to fix the calcium and the phosphorus in the form of free ions present in the HBSS medium to form an apatite layer on the surface thereof. Already after 8 hours of immersion, most of the calcium and phosphorus free ions are absorbed on the surface of the samples. These results correspond to the gravimetric recordings which indicate that the samples are heavier after 3 weeks of immersion. These results therefore indicate that the material 1 (non-enriched hydroxyapatite) fixes the calcium and the phosphorus in the form of free ions, and that the dissolution of hydroxyapatite in the HBSS medium is marginal.

These results show, for the material 2—solid phase of hydroxyapatite of natural bovine origin enriched by a synthetic solid phase of calcium phosphate (ratio 90/10)—that two phenomena take place concurrently since the calcium and phosphorus concentrations first both decrease, which is again linked to the capacity that hydroxyapatite has to fix these ions. However, the phosphorus concentration in the medium then increases and even exceeds the concentration of this compound in the initial HBSS medium, while the calcium concentration remains less than that initially measured in the HBSS medium by however being greater than that measured when the material 1 is immersed in this same medium. At the same time, after 3 weeks, the gravimetric results show that the samples have lost weight. All of these results for the material 2 indicate that this material is dissolved in the HBSS medium, which can only be attributed to the enriching phase (synthetic solid phase of calcium phosphate), since the results obtained with the material 1 show that the dissolution of hydroxyapatite under the same conditions is totally marginal.

The results obtained with the material 3—solid phase of hydroxyapatite of natural bovine origin enriched by a synthetic solid phase of calcium phosphate (ratio 80/20)—demonstrate that no decrease in calcium and phosphorus concentrations takes place, that on the contrary, since the calcium and phosphorus concentrations increase over time at the same time with a loss of weight of the samples. From these observations, it can be concluded that these increases of calcium and phosphorus concentrations are due to a dissolution of the second phase of the material 3 in the HBSS medium since the results obtained with the material 1 show that the dissolution of hydroxyapatite under the same conditions is totally marginal. Moreover, it can be observed that the material 3 does not fix the calcium and the phosphorus in the form of free ions salted-out or only marginally, which ensures that the latter remain in solution.

All of these results also show that the enriching (synthetic solid phase of calcium phosphate) is more soluble than hydroxyapatite and that it is able to salt-out the calcium and the phosphorus in the form of free ions ($Ca^{2+}$ and $PO_4^{3-}$) in the surrounding medium (HBSS imitating blood plasma).

Example 2. Bone Regeneration Material at Controlled Sintering Temperatures

A bone regeneration material has been obtained according to the present invention and consisting essentially of a hydroxyapatite solid phase. In the present example, the material has been sterilized.

Several analyses have been performed; among them the composition of the solid phase, the crystal size, the volumic porosity, the particle size, the specific surface; this has been done for three samples of the bone regeneration material.

The three samples have all 100% of hydroxyapatite, meeting the requirement of consisting essentially of hydroxyapatite.

The sample 1 has a crystal size of 54.6 nm; sample 2 of 54.2 nm and sample 3 of 54.4 nm. The median size of the crystals of the bone regeneration material according to the present invention is thus of 54.4 nm.

The volumic porosity of sample 1 is of 82.3%; sample 2: 82.1% and sample 3: 82.5%. The mean volumic porosity is thus of 82.3%.

Sample 1 has a granulometric distribution $d_{10}$ of 381 μm, $d_{50}$ of 553 μm and $d_{90}$ of 877 μm.

Sample 2 has a granulometric distribution $d_{10}$ of 452 μm, $d_{50}$ of 782 μm and $d_{90}$ of 1243 μm.

Sample 3 has a granulometric distribution $d_{10}$ of 474 μm, $d_{50}$ of 756 μm and $d_{90}$ of 1115 μm.

Hence the mean granulometric distribution $d_{10}$ is thus of 436 μm, the $d_{50}$ is of 697 μm and the $d_{90}$ is of 1079 μm.

Moreover, the bone regeneration material according to the present invention has been obtained after a sintering step at 820° C. for a duration between 45 and 60 min. (plateau), thereby allowing a more rigid and resistant bone regeneration material, having a rough surface topography, improving the bone regeneration potential.

Figure 4:
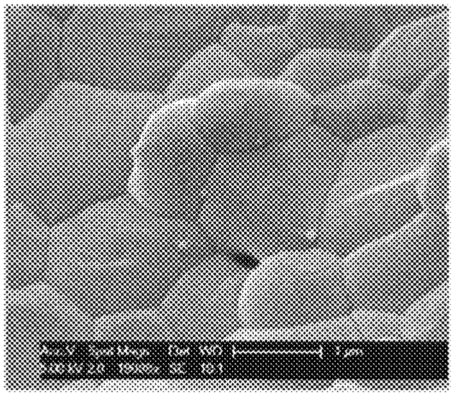
FIG. 4 illustrates an image obtained by scanning electronic microscopy of the structure of a bone regeneration material according to the prior art, sintered at a temperature above 1200° C.
Figure 5A:
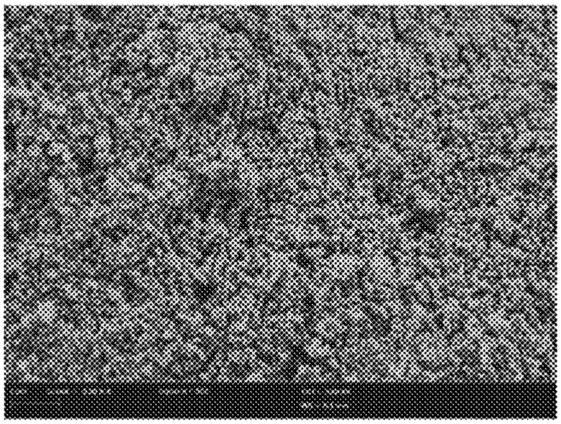
FIGS. 5*a* and 5*b* illustrates an image obtained by scanning electronic microscopy of the structure of a bone regeneration material sintered at a temperature of 820° C. at a 5000 and 10000 magnification.
Figure 5B:
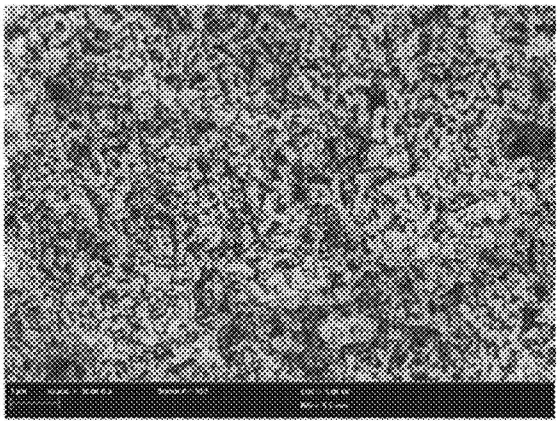

Indeed, as shown in the FIGS. 5A and 5B, the present bone regeneration material presents substantially spherical-like or ball-like elements made of hydroxyapatite, from a size between 150 and 350 nm, forming together a rough surface. This contrasts with the material shown at FIG. 4, which has been sintered at a temperature above 1200° C., which presents a smooth surface hampering the bone regeneration potential.

Example 3—Preparation of the Bone Regeneration Material According to the Present Invention A batch of bone regeneration material has been prepared in obtaining bovine bones, then in cutting them so as to form a bone material.

The bone regeneration material comprising hydroxyapatite and organic substances has been put in contact with an aqueous extraction solution under supercritical conditions, for instance between 220° C. and 230° C. and at a pressure comprised between 3200 kPa and 3500 kPa so as to obtain a first liquid phase with the organic substances, and a second solid phase of hydroxyapatite; these two phases are then separated.

The separated solid hydroxyapatite phase has been weakened by the supercritical extraction process, and is placed on a first sieve of 1 mm for a first sieving step, then on a second sieve of 0.25 mm for a second sieving step. Metallic balls have been added to help the sieving step. If needed, the sieving steps can be repeated, for instance 2 or three times.

The hydroxyapatite is then sintered at 820° C. (plateau sub-step) for 45 to 60 minutes. This forms the bone regeneration material according to the present invention, which is more rigid and more resistant and with a rough surface topography, thereby improving the bone regeneration potential.

This sintered hydroxyapatite phase can be then rinsed and/or enriched in calcium and phosphorus by distinct immersion steps, then sterilized, preferably by ionising radiation.

It is well understood that the present invention is, in no manner, limited to the embodiments described above, and that modifications can be contributed to it without moving away from the scope of the appended claims.

What is claimed is:

1. A bone regeneration material consisting of a solid phase of hydroxyapatite of natural origin which is macroporous having pores of diameters greater than or equal to 50 μm, wherein said phase of hydroxyapatite is a crystalline solid phase of hydroxyapatite, wherein the crystals have a size comprised between 20 and 120 nm, and said solid phase of hydroxyapatite has a specific surface area comprised between 8 and 20 $m^2/g$, and in which said bone regeneration material harbours spherical-like/ball-like elements of a size comprised between 150 and 350 nm forming together a rough surface.

2. The bone regeneration material according to claim 1, wherein the crystals of the solid phase of hydroxyapatite have a size comprised between 30 and 120 nm.

3. The bone regeneration material according to claim 1, wherein the specific surface area is comprised between 10 and 20 $m^2/g$.

4. The bone regeneration material according to claim 1, having a porosity comprised between 70 and 85%.

5. The bone regeneration material according to claim 1, having a granulometric distribution $d_{50}$ comprised between 500 and 800 μm.

6. The bone regeneration material according to claim 1, having a granulometric distribution $d_{90}$ comprised between 850 and 1250 μm.

7. An enriched bone regeneration material consisting of:

(i) a bone regeneration material consisting of a first solid phase of hydroxyapatite of natural origin which is macroporous having pores of diameters greater than or equal to 50 μm, wherein said phase of hydroxyapatite is a crystalline solid phase of hydroxyapatite, wherein the crystals have a size comprised between 20 and 120 nm, and said solid phase of hydroxyapatite has a specific surface area comprised between 8 and 20 $m^2/g$, and in which said bone regeneration material harbours spherical-like/ball-like elements of a size comprised between 150 and 350 nm forming together a rough surface, and (ii) a second solid phase which enriches said first solid phase, said second solid phase being a synthetic solid phase of calcium phosphate, said second phase having a Ca/P molar ratio of between 0.2 and 2, said bone regeneration material having a defined weight ratio between the first solid phase of hydroxyapatite of natural origin and said second synthetic solid phase of calcium phosphate of between 99/1 and 70/30, wherein said second synthetic solid phase of calcium phosphate having a Ks solubility product greater than that of said first solid phase of hydroxyapatite of natural origin.

8. The bone regeneration material of claim 1, wherein the solid phase of hydroxyapatite of natural origin is hydroxyapatite obtained from a bone material of natural origin.

9. The bone regeneration material of claim 1, intended to be used as an implant or prosthesis for a bone formation, a bone regeneration or for a bone correction in a mammal.

10. The bone regeneration material of claim 1 being sterile.

11. The bone regeneration material according to claim 1, wherein the crystals of the solid phase of hydroxyapatite have a size comprised between 40 and 80 nm.

12. The bone regeneration material of claim 8, wherein said bone material is of an animal origin.

13. A sterilized bone regeneration material consisting essentially of a solid phase of hydroxyapatite of natural origin which is macroporous having pores of diameters of between 50 and 100 μm, wherein said phase of hydroxyapatite is a crystalline solid phase of hydroxyapatite, wherein the crystals have a size comprised between 50 and 80 nm, and said solid phase of hydroxyapatite has a specific surface area comprised between 10 and 18 $m^2/g$, and in which said bone regeneration material having a porosity between 80 and 85%, harbours spherical-like/ball-like elements of a size comprised between 150 and 350 nm forming together a rough surface, and in which said sterilized bone regeneration material has 100% of said solid phase of hydroxyapatite.

14. A method to produce a bone regeneration material comprising the following steps:

contacting a bone material of natural origin comprising hydroxyapatite and organic substances with an extraction aqueous solution at a temperature between 150° C. and 300° C. and at a pressure comprised between 1500 kPa and 3500 kPa so as to obtain a first liquid phase comprising said organic substances and potential impurities extracted from the said bone material, and a second phase of solid hydroxyapatite, separating the said liquid phase from the said solid hydroxyapatite phase, sintering the said separated solid hydroxyapatite phase at a temperature comprised between 800° C. and 1200° C., optionally rinsing the said sintered hydroxyapatite, wherein the said sintered hydroxyapatite phase forms the said bone regeneration material, the method being for the production of a bone regeneration material consisting essentially of a solid phase of hydroxyapatite of natural origin which is macroporous having pores of diameters greater than or equal to 50 μm, wherein said phase of hydroxyapatite is a crystalline solid phase of hydroxyapatite, wherein the crystals have a size comprised between 20 and 120 nm, and said solid phase of hydroxyapatite has a specific surface area comprised between 8 and 20 $m^2/g$, and in which said bone regeneration material harbours spherical-like/ball-like elements of a size comprised between 150 and 350 nm forming together a rough surface.

15. The method according to claim 14, wherein the extraction aqueous solution is at a temperature between 170° C. and 280° C.

16. The method according to claim 14, wherein the extraction aqueous solution is at a pressure between 2000 and 3500 kPa.

17. The method according to claim 14, wherein the sintering step is performed for a period between 40 minutes and 4 hours.

18. The method according to claim 14, wherein the sintering step is performed at a temperature between 800° C. and 1150° C.

19. The method of claim 14, further comprising a sieving step, after the separation step and before the sintering step of the said solid hydroxyapatite phase.

20. The method of claim 19, wherein metallic balls are added during the sieving step and are moved on the mesh so as to improve the said sieving step.

21. The method of claim 19, further comprising, after the sieving step and before the sintering step of the said solid hydroxyapatite phase, a step of treating the solid hydroxyapatite by peroxides such as hydrogen peroxide, optionally following by a drying step of the said hydroxyapatite.

22. The method of claim 14, further comprising the step of enriching the bone regeneration material in calcium and phosphorous by at least one first and at least one second separate soaking succeeding one another in any order, said at least one first soaking taking place in a first solution comprising calcium and said at least one second soaking taking place in a second solution comprising phosphorus.

23. The method of claim 14, further comprising the step of sterilization of the bone regeneration material or of the enriched bone regeneration material.

24. A method of repair a bone defect in a patient comprising the steps of:

measuring the size of the defect to correct placing a synthetic bone regeneration device arranged to increase bone regeneration in the bone defect, being obtained by 3D printing and comprising at least one shell made of a porous matrix and presenting pores having a size comprised between 50 and 1000 μm, and at least a holder shaft bound on this porous matrix and on the bone surface of this bone defect, this device being arranged so as to encompass an empty zone, which is arranged to house a bone volume to regenerate, filling the said empty zone formed by the said device by the bone regeneration obtainable by the method of claim 14.

25. The method of claim 24 for repair of a bone subject to heavy mechanical constraints.

* * * * *